United States Patent [19]

Bergonzoni et al.

[11] Patent Number: 5,288,855
[45] Date of Patent: Feb. 22, 1994

[54] EXTRACELLULAR FORM OF THE HUMAN FIBROBLAST GROWTH FACTOR RECEPTOR

[75] Inventors: Laura Bergonzoni; Guy Mazue; Antonella Isacchi; Romeo Roncucci; Paolo Sarmientos, all of Milan, Italy

[73] Assignee: Farmitalia Carlo Erba, Milan, Italy

[21] Appl. No.: 997,133

[22] Filed: Dec. 28, 1992

Related U.S. Application Data

[63] Continuation of Ser. No. 642,755, Jan. 18, 1991, abandoned.

[30] Foreign Application Priority Data

Jan. 23, 1989 [GB] United Kingdom .............. 9001466

[51] Int. Cl.$^5$ .................. C12P 21/06; C07K 3/00; A61K 37/24; A01N 37/18
[52] U.S. Cl. .................. 530/399; 530/350; 530/351; 435/69.1; 435/240.2; 536/23.5
[58] Field of Search .......... 435/69.1, 240.2, 320.1, 435/245; 530/350, 351, 399; 536/27; 514/2, 8, 12

[56] References Cited

U.S. PATENT DOCUMENTS 4,507,234  3/1985  Kato et al. .................. 514/2

OTHER PUBLICATIONS

Isaachi et al. (1990) Nucleic Acids Research vol. 18, No. 7, p. 1906.

Pasquale et al. (1989) PNAS, vol. 86, pp. 5449–5453.
Dionne et al. (1990) The EMBO Journal vol. 9, No. 9, pp. 2685–2692.
Kornbluth, S. et al: Molecular and Cellular biology, vol. 8 No. 12, pp. 5541–5544; Dec. 1988.
Pasquale, E. B. and Singer, S. J.: Proc. Natl. Acad. Sci. USA, vol. 86, pp. 5449–5453; Jul. 1989.
Ruta, M. et al: Proc. Natl. Acad Sci. USA, vol. 86, pp. 8722–8726; Nov. 1989.
Lee, P. L. et al.: Science, vol. 245, pp. 57–60, Jul. 7, 1989.
Itoh, N. et al.: Biochem. Biophys. Res. Comm., vol. 169, No. 2, pp. 680–685, Jun. 15, 1990.
Isacchi, A. et al.: Nucleic Acids Research, vol. 18, No. 7, p. 1906, Nov. 18, 1990.

Primary Examiner—Robert J. Hill, Jr.
Assistant Examiner—Gian P. Wang
Attorney, Agent, or Firm—Oblon, Spivak, McClelland, Maier & Neustadt

[57] ABSTRACT

The present invention provides a polypeptide which is capable of binding specifically human basic fibroblast growth factor and human acidic fibroblast growth factor, a DNA sequence which encodes the polypeptide of the invention and a vector which incorporates a DNA sequence of the invention and which is capable, when provided in a transformed host, of expressing the polypeptide of the invention encoded by the DNA sequence. A host transformed with such a vector forms part of the invention also.

2 Claims, 5 Drawing Sheets

| | |
|---|---:|
| MVSWKCLLFWAVLVTATLCTARPSPTLPEQAQPWGAPVEVESFLVHPGDLLQLRCRLRDDVQSINWLRDGVQLAETNRTRITGEEV | 86 |
| EVQDSVPADSGLYACVTSSPSGSDTTYFSVNVSDALPSSEDDDDDDSSSEEKETDNTKPNRMPVAPYWTSPEKMEKKLHAVPAAK | 172 |
| TVKFKCPSSGTPNPTLRWLKNGKEFKPDHRIGGYKVRYATWSIIMDSVVPSDKGNYTCIVENEYGSINHTYQLDVVERSPHRPILQ | 258 |
| AGLPANKTVALGSNVEEMCKVYSDPQPHIQWLKHIEVNGSKIGPDNLPYVQILKTAGVNTTDKEMEVLHLRNVSFEDAGEYTCLAG | 344 |
| NSIGLSHHSAWLTVLEALEERPAVMTSPLYLEIIIYCTGAFLISQMVGSVIVYKMKSGTKKSDFHSQMAVHKLAKSIPLRRQVTVS | 430 |
| ADSSASMNSGVLLVRPSRLSSSGTPMLAGVSEYELPEDPRWELPRDRLVLGKPLGEGCFGQVVLAEAIGLDKDKPNRVTKVAVKML | 516 |
| KSDATEKDLSDLISEMEMMKMIGKHKNIINLLGACTQDGPLYVIVEYASKGNLREYLQARRPPGLEYCYNPSHNPEEQLSSKDLVS | 602 |
| CAYQVARGMEYLASKKCIHRDLAARNVLVTEDNVMKIADFGLARDIHHIDYYKKTTNGRLPVKWMAPEALFDRIYTHQSDVWSFGV | 688 |
| LLWEIFTLGGSPYPGVPVEELFKLLKEGHRMDKPSNCTNELYMMMRDCWHAVPSQRPTFKQLVEDLDRIVALTSNQEYLDLSMPLD | 774 |
| QYSPSFPDTRSSTCSSGEDSVFSHEPLPEEPCLPRHPAQLANRGLKFRTer | 822 |

FIG. 1

```
ATG TGG AGC TGG AAG TGC CTC CTC TTC TGG GCT GTG CTG GTC ACA      45
GCC ACA CTC TGC ACC GCT AGG CCG TCC CCG ACC TTG CCT GAA CAA      90
GCC CAG CCC TGG GGA GCC CCT GTG GAA GTG GAG TCC TTC CTG GTC      135
CAC CCC GGT GAC CTG CTG CAG CTT CGC TGT CGG CTG CGG GAC GAT      180
GTG CAG AGC ATC AAC TGG CTG CGG GAC GGG GTG CAG CTG GCG GAA      225
AGC AAC CGC ACC CGC ATC ACA GGG GAG GAG GTG GAG GTG CAG GAC      270
TCC GTG CCC GCA GAC TCC GGC CTC TAT GCT TGC GTA ACC AGC AGC      315
CCC TCG GGC AGT GAC ACC ACC TAC TTC TCC GTC AAT GTT TCA GAT      360
GCT CTC CCC TCC TCG GAG GAT GAT GAT GAT GAT GAT GAC TCC TCT      405
TCA GAG GAG AAA GAA ACA GAT AAC ACC AAA CCA AAC CGT ATG CCC      450
GTA GCT CCA TAT TGG ACA TCC CCA GAA AAG ATG GAA AAG AAA TTG      495
CAT GCA GTG CCG GCT GCC AAG ACA GTG AAG TTC AAA TGC CCT TCC      540
AGT GGG ACC CCA AAC CCC ACA CTG CGC TGG TTG AAA AAT GGC AAA      585
GAA TTC AAA CCT GAC CAC AGA ATT GGA GGC TAC AAG GTC CGT TAT      630
GCC ACC TGG AGC ATC ATA ATG GAC TCT GTG GTG CCC TCT GAC AAG      675
GGC AAC TAC ACC TGC ATT GTG GAG AAT GAG TAC GGC AGC ATC AAC      720
CAC ACA TAC CAG CTG GAT GTC GTG GAG CGG TCC CCT CAC CGG CCC      765
ATC CTG CAA GCA GGG TTG CCC GCC AAC AAA ACA GTG GCC CTG GGT      810
AGC AAC GTG GAG TTC ATG TGT AAG GTG TAC AGT GAC CCG CAG CCG      855
CAC ATC CAG TGG CTA AAG CAC ATC GAG GTG AAT GGG AGC AAG ATT      900
GGC CCA GAC AAC CTG CCT TAT GTC CAG ATC TTG AAG ACT GCT GGA      945
GTT AAT ACC ACC GAC AAA GAG ATG GAG GTG CTT CAC TTA AGA AAT      990
GTC TCC TTT GAG GAC GCA GGG GAG TAT ACG TGC TTG GCG GGT AAC      1045
TCT ATC GGA CTC TCC CAT CAC TCT GCA TGG TTG ACC GTT CTG GAA      1080
GCC CTG GAA GAG AGG CCG GCA GTG ATG ACC TCG CCC CTG TAC CTG      1125
GAG ATC ATC ATC TAT TGC ACA GGG GCC TTC CTC ATC TCC TGC ATG      1170
GTG GGG TCG GTC ATC GTC TAC AAG ATG AAG AGT GGT ACC AAG AAG      1215
AGT GAC TTC CAC AGC CAG ATG GCT GTG CAC AAG CTG GCC AAG AGC      1260
ATC CCT CTG CGC AGA CAG GTA ACA GTG TCT GCT GAC TCC AGT GCA      1305
```

*FIG. 2A*

```
TCC ATG AAC TCT GGG GTT CTT CTG GTT CGG CCA TCA CGG CTC TCC     1350
TCC AGT GGG ACT CCC ATG CTA GCA GGG GTC TCT GAG TAT GAG CTT     1395
CCC GAA GAC CCT CGC TGG GAG CTG CCT CGG GAC AGA CTG GTC TTA     1440
GGC AAA CCC CTG GGA GAG GGC TGC TTT GGG CAG GTG GTG TTG GCA     1485
GAG GCT ATC GGG CTG GAC AAG GAC AAA CCC AAC CGT GTG ACC AAA     1530
GTG GCT GTG AAG ATG TTG AAG TCG GAC GCA ACA GAG AAA GAC TTG     1575
TCA GAC CTG ATC TCA GAA ATG GAG ATG ATG AAG ATG ATC GGG AAG     1620
CAT AAG AAT ATC ATC AAC CTG CTG GGG GCC TGC ACG CAG GAT GGT     1665
CCC TTG TAT GTC ATC GTG GAG TAT GCC TCC AAG GGC AAC CTG CGG     1710
GAG TAC CTG CAG GCC CGG AGG CCC CCA GGG CTG GAA TAC TGC TAC     1755
AAC CCC AGC CAC AAC CCA GAG GAG CAG CTC TCC TCC AAG GAC CTG     1800
GTG TCC TGC GCC TAC CAG GTG GCC CGA GGC ATG GAG TAT CTG GCC     1845
TCC AAG AAG TGC ATA CAC CGA GAC CTG GCA GCC AGG AAT GTC CTG     1890
GTG ACA GAG GAC AAT GTG ATG AAG ATA GCA GAC TTT GGC CTC GCA     1935
CGG GAC ATT CAC CAC ATC GAC TAC TAT AAA AAG ACA ACC AAC GGC     1980
CGA CTG CCT GTG AAG TGG ATG GCA CCC GAG GCA TTA TTT GAC CGG     2025
ATC TAC ACC CAC CAG AGT GAT GTG TGG TCT TTC GGG GTG CTC CTG     2070
TGG GAG ATC TTC ACT CTG GGC GGC TCC CCA TAC CCC GGT GTG CCT     2115
GTG GAG GAA CTT TTC AAG CTG CTG AAG GAG GGT CAC CGC ATG GAC     2160
AAG CCC AGT AAC TGC ACC AAC GAG CTG TAC ATG ATG ATG CGG GAC     2205
TGC TGG CAT GCA GTG CCC TCA CAG AGA CCC ACC TTC AAG CAG CTG     2250
GTG GAA GAC CTG GAC CGC ATC GTG GCC TTG ACC TCC AAC CAG GAG     2295
TAC CTG GAC CTG TCC ATG CCC CTG GAC CAG TAC TCC CCC AGC TTT     2340
CCC GAC ACC CGG AGC TCT ACG TGC TCC TCA GGG GAG GAT TCC GTC     2385
TTC TCT CAT GAG CCG CTG CCC GAG GAG CCC TGC CTG CCC CGA CAC     2430
CCA GCC CAG CTT GCC AAT CGG GGA CTC AAA CGC CGC TGA             2469
```

*FIG. 2B*

```
MWSWKCLLFWAVLVTATLCTARPSPTLPEDAQPWGAPVEVESFLVHPGDLLQLRCRLRDDVQSINWLRDGVQLAETNRTRITGEEV      86
EVQDSVPADSGLYACVTSSPSGSDTTYFSVNVSDALPSSEDDDDDDSSEEKETDNTKPNRMPVAPYWTSPEKMEKKLHAVPAAK      172
TVKFKCPSSGTPNPTLRWLKNGKEFKPDHRIGGYKVRYATWSIIMDSVVPSDKGNYTCIVENEYGSINHTYQLDVVERSPHRPILQ     258
AGLPANKTVALGSNVEEMCKVYSDPQPHIQWLKHIEVNGSKIGPDNLPYVDILKTAGVNTTDKEMEVLHLRNVSFEDAGEYTCLAG     344
NSIGLSHHSAWLTVLEALEERPAVMTSPLYLEIIIYCTGAFLISDMVGSVIVYKMKSGTKKSDFHSQMAVHKLAKSIPLRRQVTVS     430
ADSSASMNSGVLLVRPSRLSSSGTPMLAGVSEYELPEDPRWELPRDRLVLGKPLGEGCFGQVVLAEAIGLDKKPNRVTKVAVKML      516
KSDATEKQLSDLISEMEMMKMIGKHKNIINLLGACTQDGPLYVIVEYASKGNLREYLQARRPPGLEYCYNPSHNPEEQLSSKDLYS     602
CAYQVARGMEYLASKKCIHRDLAARNVLVTEDNVMKIADFGLARDIHHIDYYKKTTNGRLPVKWMAPEALFDRIYTHQSDVWSFGV     688
LLWEIFTLGGSPYPGVPVEELFKLLKEGHRMDKPSNCTNELYMMMRDCWHAVPSQRPTFKQLVEDLDRIVALTSNQEYLDLSMPLD     774
QYSPSFPDTRSSTCSSSGEDSVFSHEPLPEEPCLPRHPAQLANRGLKFRTer                                       822
```

EXTRACELLULAR FORM OF THE HUMAN FIBROBLAST GROWTH FACTOR RECEPTOR

This application is a continuation of application Ser. No. 07/642,755, filed on Jan. 18, 1991, now abandoned.

BACKGROUND OF THE INVENTION

The present invention relates to human growth factor receptors.

The formation of blood capillaries occurs in a number of important biological processes, either physiological, such as organ development and wound healing, or pathological, such as tumor growth. While the sequence of events leading to neovascularization has been characterized morphologically, the molecular mechanisms by which this process occurs are still poorly understood. The control of growth in the capillary endothelium appears to be very tightly controlled, since these cells normally form a static monolayer whose proliferation is triggered in the angiogenic process. The normally quiescent nature of the endothelial cells may be explained in part by the apparent lack of endothelial cell growth factors to plasma. The major endothelial cell mitogens in fact are not found in plasma, although they are present in extracts of almost all tissues studied and in many normal and tumor cell lines as well. Therefore, the localized induction of rapid endothelial cell proliferation may involve the release of endothelial cell mitogens from cells in response to environmental cues.

The best characterized of the endothelial cell mitogens are a family of polypeptide growth factors, including basic fibroblast growth factor (bFGF), also known as heparin-binding growth factors for their high affinity to heparin. Basic FGF has been purified from most mesoderm- or neuroectoderm-derived tissues or cells. Structural studies have shown that bFGF is a single chain polypeptide made of 146 amino acids, which can also exist in $NH_2$-terminally truncated forms missing the first 10-20 amino acids. The truncated forms of bFGF are as potent as native bFGF, as demonstrated by radioreceptor binding and biological assays. In addition, modifications of the purification protocols by substitution of neutral for acidic extraction from homogeneized tissue and inclusion of protease inhibitors have yielded a longer 154-residue form. The observed microheterogeneity of FGFs seems to be due, at least in part, to partial proteolysis near the amino termini that occurs either in vivo or during purification. However, because the various forms appear to be equally active, the microheterogeneity is probably physiologically irrelevant.

Basic FGF seems to have been extremely well conserved through evolution. For example, bovine and human bFGF differ in only two of their 146 amino acids, giving an overall amino acid sequence homology of 98.7%. Related to bFGF is acidic FGF (aFGF), which shares a 55% total sequence homology with bFGF. Acidic FGF is a 140-amino acid polypeptide that can also exist in a $NH_2$-terminally truncated form missing the first 6 amino acids. As expected from their high degree of homology, both basic and acidic FGF seem to interact with the same cell-surface receptors. This explains their common range of target cells and spectrum of biological activity.

Recently, Lee et al (Science, 245, 57-60, 1989) have described the purification, from chicken embryos, of a new membrane protein able to bind specifically basic FGF. On the base of its biochemical characteristics and on homology with other known receptors, this new protein is thought to be a basic FGF receptor. In the same article the authors describe the isolation of a chicken full-length cDNA clone coding for the described protein. The nucleotide sequence of this clone is however not disclosed.

Lee et al noted that the chicken bFGF receptor shows a considerable amino acid similarity to a previously identified human polypeptide sequence which is the product of the flg gene (Ruta et al, Oncogene, 3, 9–15, 1988). Like the chicken bFGF receptor, the flg molecule seems to be a tyrosine kinase, shows a typical hydrophobic transmembrane region and consequently it is likely that the described human sequence could be part of the human bFGF receptor.

The amino acid sequence of the flg molecule was deduced by Ruta et al by the translation of an open reading frame of a partial cDNA clone. The flg cDNA sequence, according to Rutal et al was obtained by low-stringency screening of a human endothelial cell cDNA library using as probe a DNA fragment coding for a tyrosine kinase oncogene. Nevertheless, the flg cDNA clone, described to date, is only partial and lacks the nucleotide sequence coding for the extracellular portion of the human bFGF receptor.

In summary, the only amino acid or nucleotide sequences available prior to the present invention were those corresponding to the complete chicken bFGF receptor and to a portion of the human basic FGF receptor. The complete extracellular amino acid sequence of the human bFGF receptor, which is responsible for the specific binding of human basic and acidic FGFs, was unknown.

SUMMARY OF THE INVENTION

Figure 3:
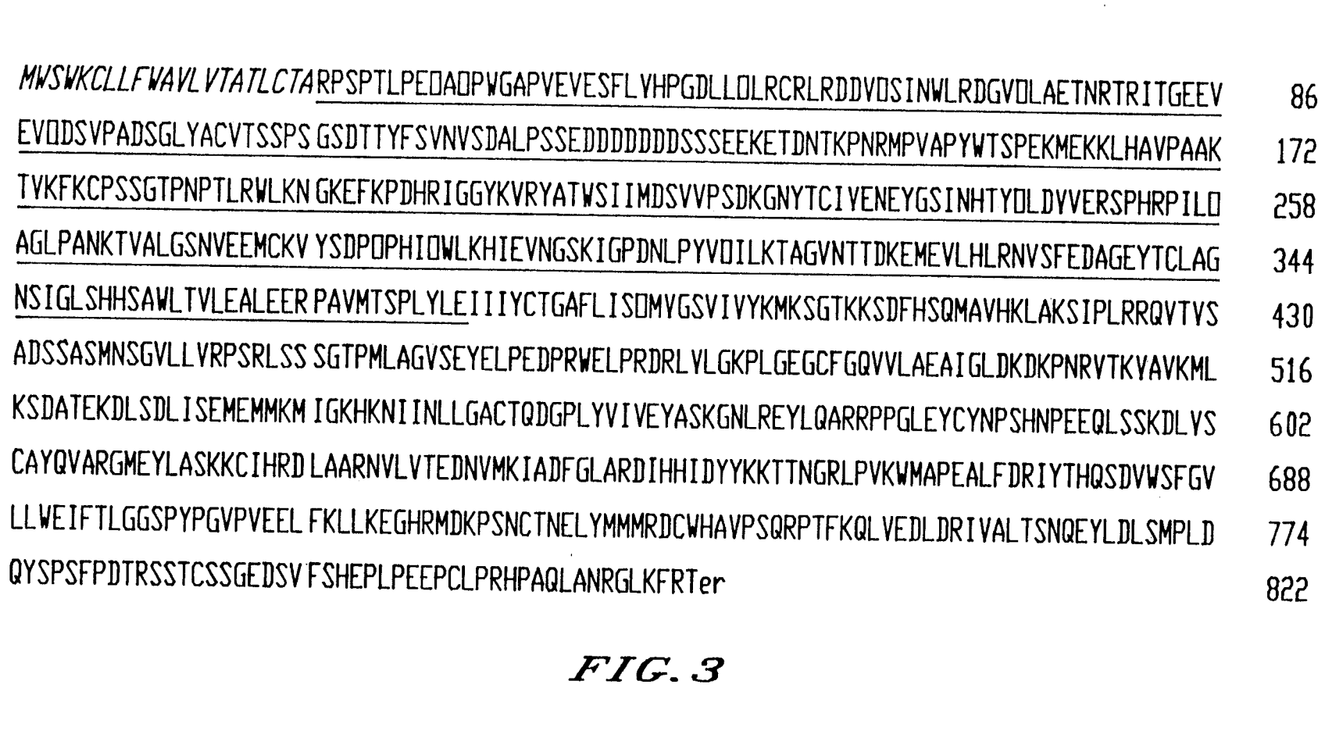
FIG. 3 [SEQ ID NO:1] shows the amino acid sequence of the bFGF receptor. The putative leader peptide is in italic characters. The previously unknown extracellular portion is underlined. The arginine (R) residue which is thought to be the first amino acid of the mature molecule is in a bold character.

We have now cloned the human bFGF receptor and have identified its extracellular portion. The receptor and its extracellular portion may be used as antagonists for bFGF or aFGF. Accordingly, the present invention provides a polypeptide which is capable of binding specifically human basic fibroblast growth factor (bFGF) and human acidic fibroblast growth factor (aFGF) and which has:

(a) the sequence shown in FIG. 3 [SEQ ID NO: 1] or a part of the said sequence or (b) a said sequence (a) modified by one or more amino acid substitutions, insertions and/or deletions and/or by an extension at either or each end.

A preferred polypeptide has:

($a_1$) the sequence underlined in FIG. 3 [SEQ ID NO: 1] or a part of the said underlined sequence or ($b_1$) a said sequence ($a_1$) modified by one or more amino acid substitutions, insertions and/or deletions and/or by an extension at either or each end.

The invention also provides a DNA sequence which encodes a polypeptide of the invention. The DNA sequence may be:

($a_2$) the sequence shown in FIG. 2 [SEQ ID NO: 2] or a part of the said sequence or ($b_2$) a said sequence ($a_2$) modified by one or more nucleotide substitutions, insertions and/or deletions and/or by an extension at either or each end.

A suitable DNA sequence is ($a_3$) the sequence from nucleotide 64 to nucleotide 1128 shown in FIG. 2 or a part of the said sequence or (b3) a said sequence (a3) modified by one or more nucleotide substitutions, insertions and/or deletions and/or by an extension at either or each end.

The invention further provides a vector which incorporates a DNA sequence of the invention and which is capable, when provided in a transformed host, of expressing the polypeptide of the invention encoded by the DNA sequence. A host transformed with such a vector forms part of the present invention too.

A polypeptide of the invention is prepared by a process which comprises culturing a transformed host according to the invention under such conditions that the polypeptide is expressed. The polypeptide can then be isolated. The polypeptide may be recovered in biologically pure form.

BRIEF DESCRIPTION OF THE DRAWINGS

FIGS. 2A and 2B [SEQ ID NO:2] show the nucleotide sequence of the bFGF receptor molecule.

The polypeptide of the invention having the sequence shown in FIG. 3 [SEQ ID NO:1] is therefore the human bFGF receptor. A polypeptide which is composed of part of the sequence shown in FIG. 3 and which is capable of binding specifically human bFGF and human aFGF also forms part of the invention. Other polypeptides of the invention are polypeptides which comprise modified versions of the sequence shown in FIG. 3 or of part of the sequence of FIG. 3 and which are capable of binding specifically human bFGF and human aFGF. For a suitable receptor-binding test, see Dower et al, J. Immunol. 42, 4314–4320, 1989.

A preferred polypeptide is the polypeptide having the sequence from amino acid 1 to amino acid 376 shown in FIG. 3. This is the sequence of the extracellular portion of the bFGF receptor with the putative leader sequence. Another preferred polypeptide is the polypeptide having the sequence underlined in FIG. 3 from amino acid 22 to amino acid 376. This is the sequence of the extracellular portion of the bFGF receptor without the putative leader sequence.

The sequence, or an appropriate part of the sequence, shown in FIG. 3 may be modified by one or more amino acid substitutions, insertions and/or deletions and/or by an extension at either or each end. A polypeptide composed of such a modified sequence must of course still be capable of binding human bFGF and aFGF. When the sequence or a part of the sequence shown in FIG. 3, i.e. an unmodified sequence is modified typically there is a degree of homology of 75% or more between the modified sequence and the unmodified sequence. The degree of homology may be 85% or more or 95% or more.

For example, one or more amino acid residues of the sequence or a part of the sequence shown in FIG. 3 may be substituted or deleted or one or more additional amino acid residues may be inserted; provided the physicochemical character of the original sequence is preserved, i.e. in terms of charge density, hydrophobicity/hydrophilicity, size and configuration. Candidate substitutions are, based on the one-letter code (Eur. J. Biochem. 138, 9–37, 1984):

A for G and vice versa,
V by A, L or G;
K by R;
S by T and vice versa;
E for D and vice versa; and
Q by N and vice versa.

As far as extensions are concerned, a short sequence of up to 50 amino acid residues may be provided at either or each terminal. The sequence may have up to 30, for example up to 20 or up to 10, amino acid residues. Alternatively, a much longer extension may be present. Longer amino acid sequences may be fused to either or each end. A chimaeric protein may therefore be provided in which the or each extension is a heterologous amino acid sequence, i.e. a sequence not naturally linked to the sequence derived from FIG. 3. Such a chimaeric protein may therefore combine the ability to bind specifically to bFGF and aFGF with another functionality.

The polypeptides are prepared by recombinant DNA technology. The preparation of the polypeptides therefore depends upon the provision of a DNA sequence encoding the polypeptide. DNA having the sequence shown in FIG. 2 may be obtained by probing a human placenta cDNA library, for example a λgt11 library. Such a library is available from Clontech. Suitable probes are:

ATAACGGACCTTGTAGCCTCCAATTCTGTG, [SEQ ID NO:3]
GGGTCTCTGTGAGGGCACTGCATGCCAGCA [SEQ ID NO:4], and
ACGGCCTAGCGGTGCAGAGTGTGGCTGTGA [SEQ ID NO:5].

A shorter sequence than that shown in FIG. 2A and 2B may be obtained by use of restriction endonucleases and/or exonucleases. A DNA sequence from nucleotide 1 to nucleotide 1128 or from nucleotide 64 to nucleotide 1128 may be provided. Modified sequences may be obtained by use of any appropriate technique, including restriction with an endonuclease, insertion of linkers, use of an exonuclease and/or a polymerase and site-directed mutagenesis. Whether a shortened and/or modified DNA sequence encodes a polypeptide of the invention can be readily ascertained. The polypeptide encoded by the sequence can be expressed in a suitable host and tested for its ability to bind specifically human bFGF and aFGF.

For expression of a polypeptide of the invention, an expression vector is constructed. An expression vector is prepared which comprises a DNA sequence encoding a polypeptide of the invention and which is capable of expressing the polypeptide when provided in a suitable host. Appropriate transcriptional and translational control elements are provided, including a promoter for the DNA sequence, a transcriptional termination site, and translational start and stop codons. The DNA sequence is provided in the correct frame such as to enable expression of the polypeptide to occur in a host compatible with the vector.

The expression vector is then provided in an appropriate host. Cells harbouring the vector are grown so as to enable expression to occur. The vector may be a plasmid or a viral vector. Any appropriate host-vector system may be employed.

The transformed host may be a prokaryotic or eukaryotic host. A bacterial or yeast host may be employed, for example E. coli or S. cerevisiae. Insect cells can alternatively be used, in which case a baculovirus expression system may be appropriate. As a further alternative, cells of a mammalian cell line, such as Chinese Hamster Overy (CHO) cells may be transformed.

The polypeptide of the invention can be isolated and purified. The polypeptide can be employed as a human bFGF or aFGF antagonist. It may sequester bFGF in vivo, thus preventing the biological activity of bFGF and acting as an inhibitor of bFGF activities. Antagonists of bFGF and aFGF activities could have clinical applications in several pathologies related to abnormal angiogenesis such as diabetic, retinopathy, neovascular glaucoma, rheumatoid arthritis, psoriasis, artherosclerosis and as contraceptives. In addition, the observation that certain solid tumors require neovascularization to grow suggests that FGF antagonists could be therapeutically developed to treat these diseases.

For this purpose, a polypeptide of the present invention may be chemically coupled to another material to provide a conjugate. The other material may be a carrier molecule or a molecule with another biological function. The polypeptide of the invention may also be formulated in a pharmaceutical composition. The pharmaceutical composition also comprises a pharmaceutically acceptable carrier or diluent. The pharmaceutical composition may contain the polypeptide of the invention in the form of a conjugate.

The polypeptide of the invention may be administered to a patient be any convenient route. The choice of whether an oral route or a parenteral route, such as subcutaneous, intravenous or intramuscular administration, is adopted; of the dose; and of the frequency of administration depends upon a variety of factors. These factors include the purpose of the administration, the age and weight of the patient being treated and the condition of the patient. Typically, however, the polypeptide is administered in an amount of from 1 to 1000 μg per dose, more preferably from 10 to 100 μg per dose, for each route of administration.

EXAMPLES

The following example illustrates the invention.

EXAMPLE 1

A cDNA clone coding for basic FGF receptor was isolated by screening a human placenta λgt11 cDNA library. This library is commercially available from Clontech.

A partial cDNA clone thought to encode a portion of the human bFGF receptor was already published in the literature (Ruta et al, 1988). According to this article, we designed two oligonucleotide probes with the following sequences:

5'       ATAACGGACCTTGTAGCCT-CCAATTCTGTG 3' [SEQ ID NO:3] (named OAB965) and

5'       GGGTCTCTGTGAGGGCACTGCATG-CCAGCA 3' [SEQ ID NO:4] (named OAB984).

A first screening was carried out using only the probe OAB965. The oligonucleotide was kinased using ($\gamma^{32}$P)ATP and purified on a Nensorb column (Nen). Following the determination of the cDNA library titre ($2 \times 10^9$ pfu/ml), appropriate dilutions were made and plated using the E. coli strain Y1090. 0.05 ml of an overnight culture of Y1090 were mixed with 0.1 ml of sterile lambda diluent (10 mM Tris HCl pH 7.5, 10 mM $MgCl_2$, 0.1 mM EDTA) containing a $4 \times 10^{-3}$ dilution of the library and incubated at 37° C. for 15 minutes to allow phage adsorption. Plating was carried out on 20 Petri dishes of LB containing ampicillin 100 μg/ml.

According to published procedures (Maniatis et al, Molecular cloning: a laboratory manual, Cold Spring Harbor Laboratory, Cold Spring Harbor, New York 1982) $10^6$ plaques were transferred onto nitrocellulose filters and hybridized under low stringency conditions (5× SSC, 0.1% SDS, 5× Denhardt solution, 0.1 mg/ml salmon sperm DNA), overnight at 65° C. The labelled probe was added at $10^6$ cpm/ml. Washes were performed at 65° C. in 6× SSC, 0.1% SDS and in 3× SSC, 0.1% SDS. Three positive clones, named PL3, PL10, and PL16 were detected after an overnight exposure with Emersham Hyperfilm-MP. These positive signals were confirmed in a separate screening using the same probe.

A second screening was then performed on PL3, PL10 and PL16 on duplicate filters using the two probes OAB 965 and OAB 984. Interestingly, these clones were recognized by both probes.

The three clones were plaque-purified and further analyzed. Phage DNA of PL3, PL10, and PL16 was purified using Lambdasorb phage adsorbent (Promega) and digested with EcoRI. From the different digestions, we selected two inserts of 2.8 Kb and 0.6 Kb from PL10 and subcloned them into M13mp19.

Nucleotide sequence analysis was carried out by primed DNA synthesis on single-stranded DNA templates in the presence of dideoxynucleoside triphosphates (Sanger et al, Proc. Natl. Acad. Sci. USA 74, 5463–5467, 1977) by using Sequenase (United States Biochemical Corp. Cleveland, Ohio). Both strands of the subclones were sequenced using either universal or specific primer oligonucleotides based on the generated sequence.

Figure 1:
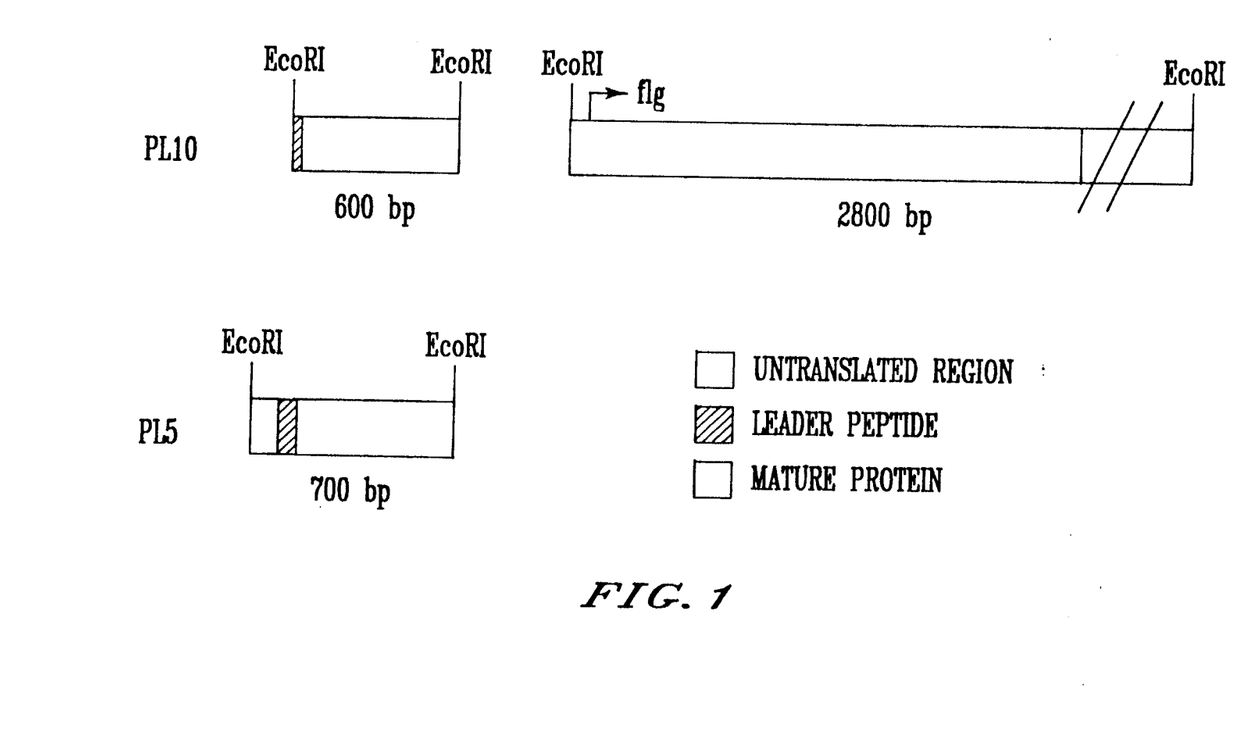
FIG. 1 is a schematic illustration of clones PL5 and PL10.

A single open reading frame for 817 amino acids with a termination codon could be detected. The first 196 amino acids of the mature bFGF receptor are codified by the insert of 0.6 kb. The final sequence of this fragment contains an EcoRI site, so that the 626 amino acids of the COOH-terminus are codified by the 2.8 Kb insert and followed by a 3' end untranslated region, as schematically illustrated in FIG. 1.

The chicken receptor for bFGF, as it has been described by Lee et al (1989), is a protein of 819 amino acids including a leader peptide of 21 amino acids, followed by a mature protein of 798 amino acids. By homology to this sequence, our clone contained the complete mature bFGF receptor molecule, preceded by 16 amino acids of the leader peptide. In order to find the remaining 5 amino acids of the leader peptide, including the starting methionine, we synthesized a new oligonucleotide probe with the following sequence, derived from the 0.6 kb insert of PL10:

5'       ACGGCCTAGCGGT-GCAGAGTGTGGCTGTGA 3' [SEQ ID NO: 5] (named OAB 1088)

By screening the library with this probe, we selected a new clone, name PL5, which contained a 0.7 kb EcoRI fragment. This fragment was sequenced and found to contain the 0.6 kb sequence from PL10, while it further extended at the 5' end. More precisely, the 0.7 kb sequence from PL5 codes for the 196 amino acids of the $NH_2$ terminal sequence, also found in PL10, preceded by 21 amino acids of the leader peptide, starting with a methionine. A schematic description of clones PL5 and PL10 is illustrated in FIG. 1.

The full length DNA sequence for a bFGF receptor, as obtained from the two overlapping clones PL5 and PL10, is depicted in FIG. 2A and 2B. The corresponding amino acid sequence is depicted in FIG. 3. In this sequence, the putative leader peptide of 21 amino acids is in italics. The arginine (R) residue which is thought to be the first amino acid of the mature molecule is in bold character. The previously unknown extracellular portion is underlined.

The full length clone and the extracellular domain have been expressed in both mammalian and bacterial cells. Cross-linking experiments with labelled basic and acidic FGFs have shown that the recombinant complete receptor and extracellular portion are indeed able to bind specifically basic and acidic FGF.

EXAMPLE 2

To obtain the expression of the extracellular portion of the human FGF receptor in *E. coli*, a vector was constructed using as regulatory signals the tryptophan promoter of *E.coli* and the ribosome binding site region of the lambda CII protein (Hendrix R. W., Roberts J. W., Stahl F. W. and Weisberg R. A.: Lambda II Cold Spring Harbour Laboratory, Cold Spring Harbour, N.Y. 1983). The 5' end of the receptor sequence was synthetically reconstructed to be cloned into the expression vector. For this purpose a HindIII-PstI synthetic DNA fragment coding for the CII ribosome binding site followed by the ATG codon and the first 95 nucleotides of the mature receptor sequence (FIG. 2A: nucleotides 61 to 155) was synthesized using complementary oligonucleotides. The complete sequence [SEQ ID NO: 6] of such synthetic fragment is:

5' AGCTTGGGCATACATTCAATCAATTGTTATCTAAGGAAATACTTAC
ATATGGCTAGGCCGTCCCCGACCTTGCCTGAACAAGCCCAGCCCTGGGG
AGCCCCTGTGGAAGTGGAGTCCTTCCTGGTCCACCCCGGTGACCTGCT
GCA 3'

Figure 4:
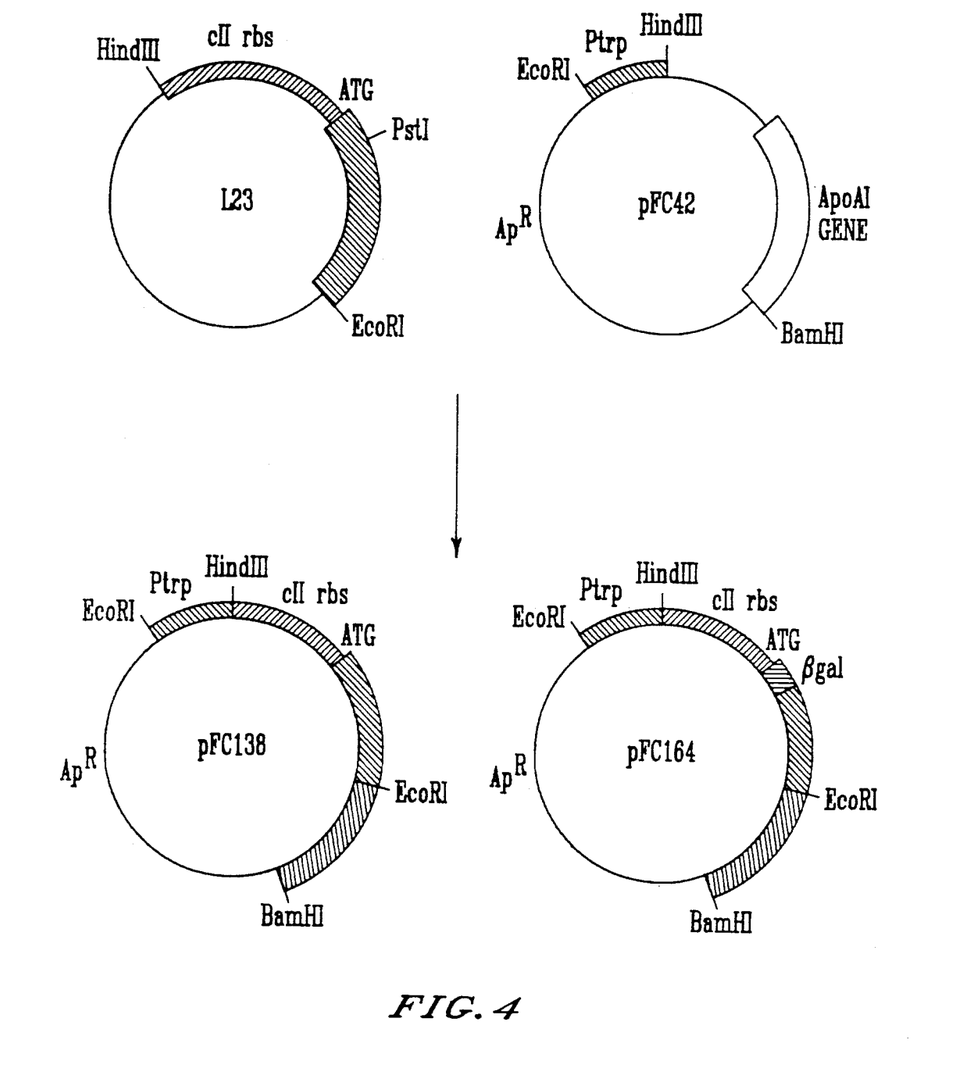
FIG. 4 shows the two intermediate constructions (plasmids L23 and pFC42) as well as the two final expression plasmids (pFC138 and pFC164) carrying the sequence coding for the extracellular form of the FGF receptor. For details, see Example 2 below.

This HindIII-PstI fragment was subcloned into M13mp18 previously cut with HindIII and EcoRI, together with a PstI-EcoRI fragment from PL5, harbouring the receptor sequence corresponding to nucleotides 156 to 586 of FIG. 2A. The resulting plasmid L23 carries the CII ribosome binding site followed by nucleotides 61 to 586 of the receptor sequence (See FIG. 4), corresponding to the first 175 amino acids of the mature protein. To obtain the whole extracellular portion of the FGF receptor an EcoRI-BamHI fragment was recovered by polymerase chain reaction (PCR) on PL10. The reaction was performed in a Perkin Elmer DNA thermal cycler, using the Perkin Elmer Amplitaq DNA Polymerase and the following cycles: 2'30" at 94° C., 30 cycles made by one step of 1'30" at 94° C. and a second step of 2'30" at 72° C. and a final cycle of 7' at 72° C. The primers used for the reaction, called OAB 1192 and OAB 1195, were the following:

OAB 1192: 5' GTAAAACGACGGCCAGT 3' [SEQ ID NO: 7]

OAB 1195: 5' ATGAGGATCCTCACTCCAGG-TACAGGGGCGAGGTCA 3' [SEQ ID NO: 8]

The amplified product was digested with EcoRI and BamHI to obtain a fragment of 546 bp, corresponding in FIG. 2A to nucleotides 587 to 1128 of the mature receptor sequence. The expression plasmid for the mature extracellular receptor protein, named pFC138, was constructed by joining the following three fragments:
1) The HindIII-EcoRI fragment from L23.
2) The EcoRI-BamHI fragment from PL10.
3) The HindIII-BamHI large fragment from plasmid pFC42, previously obtained in our laboratory (Isacchi A., Sarmientos P., Lorenzetti R. and Soria M.: Mature apolipoprotein AI and its precursor proApo AI: influence of the sequence at the 5' end of the gene on the efficiency of expression in *Escherichia coli*. Gene 81 p. 129–137 1989), harbouring the tryptophan promoter and the β-lactamase gene for resistance to ampicillin.

An *E.coli* B strain (Delbruck M.: Bacterial viruses or bacteriophages. Biol.Rev. 21 p. 30–40 1946) was used for expression of the mature extracellular FGF receptor protein. Induction and analysis of protein expression were performed as described (Isacchi A. et al.). The protein was recognized in western blot by rabbit anti-human FGF receptor polyclonal antibodies (Promega).

Alternatively, to optimize protein production and intracellular stability, the recombinant extracellular domain could be synthesized as a protein fusion, where additional amino acid residues are present either at the $NH_2$-end or at the COOH-end of the mature extracellular region. As an example of such fusion approach we have constructed a new plasmid named pFC164 shown in FIG. 4, where the amino acids 9 to 23 of the *E.coli* β-galactosidase were inserted upstream of the mature extracellular domain. This plasmid was constructed in a way similar to pFC138 and, when introduced in the *E.coli* host strain B, yields expression of the desired fusion protein. Cultivation of the recombinant strain and product analysis are carried out as already described for the non-fusion product.

---

We claim:

1. A polypeptide which is capable of binding specifically human basic fibroblast growth factor and human acidic fibroblast growth factor and which consists of the sequence underlined in FIG. 3.

2. A composition comprising a pharmaceutically acceptable carrier or diluent and, as an active principle, a polypeptide as claimed in claim 1.

* * * * *

UNITED STATES PATENT AND TRADEMARK OFFICE
CERTIFICATE OF CORRECTION

PATENT NO. : 5,288,855
DATED : February 22, 1994
INVENTOR(S) : Laura BERGONZONI, et al.

It is certified that error appears in the above-indentified patent and that said Letters Patent is hereby corrected as shown below:

On the title page, Item [30], the Foreign Application Priority Data should read as follows:

--Jan. 23, 1990 [GB]  United Kingdom ............9001466--

Signed and Sealed this

Twenty-eighth Day of June, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,288,855                         Page 1 of 2
DATED        : February 22, 1994
INVENTOR(S)  : Laura BERGONZONI, et al It is certified that error appears in the above-indentified patent and that said Letters Patent is hereby corrected as shown below:

The figure on title page and figure 3 on drawing sheet, should read as follows:

Amino Acid position 30 should be changed from "O" to --Q--;

Amino Acid position 32 should be changed from "O" to --Q--;

Amino Acid position 52 should be changed from "O" to --Q--;

Amino Acid position 62 should be changed from "O" to --Q--;

Amino Acid position 72 should be changed from "O" to --Q--;

Amino Acid position 89 should be changed from "O" to --Q--;

Amino Acid position 244 should be changed from "O" to --Q--;

Amino Acid position 258 should be changed from "O" to --Q--;

Amino Acid position 275 should be changed from "E" to --F--;

UNITED STATES PATENT AND TRADEMARK OFFICE
CERTIFICATE OF CORRECTION

PATENT NO. : 5,288,855
DATED : February 22, 1994
INVENTOR(S) : Laura BERGONZONI, et al It is certified that error appears in the above-indentified patent and that said Letters Patent is hereby corrected as shown below:

Amino Acid position 284 should be changed from "O" to --Q--;

Amino Acid position 288 should be changed from "O" to --Q--;

Amino Acid position 309 should be changed from "O" to --Q--;

Amino Acid position 389 should be changed from "O" to --C--.

Signed and Sealed this

Twenty-ninth Day of November, 1994

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:

-continued (A) LENGTH: 822 amino acids
(B) TYPE: amino acid
(D) TOPOLOGY: linear (ii) MOLECULE TYPE: protein (xi) SEQUENCE DESCRIPTION: SEQ ID NO:1:

```
Met Trp Ser Trp Lys Cys Leu Leu Phe Trp Ala Val Leu Val Thr Ala
 1               5                  10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Thr Asn Arg Thr Arg
 65                 70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400
```

```
Ser Gly Thr Lys Lys Ser Asp Phe His Ser Gln Met Ala Val His Lys
            405             410                 415
Leu Ala Lys Ser Ile Pro Leu Arg Arg Gln Val Thr Val Ser Ala Asp
            420             425                 430
Ser Ser Ala Ser Met Asn Ser Gly Val Leu Leu Val Arg Pro Ser Arg
            435             440                 445
Leu Ser Ser Ser Gly Thr Pro Met Leu Ala Gly Val Ser Glu Tyr Glu
    450             455                 460
Leu Pro Glu Asp Pro Arg Trp Glu Leu Pro Arg Asp Arg Leu Val Leu
465             470                 475                     480
Gly Lys Pro Leu Gly Glu Gly Cys Phe Gly Gln Val Val Leu Ala Glu
                485                 490                     495
Ala Ile Gly Leu Asp Lys Asp Lys Pro Asn Arg Val Thr Lys Val Ala
            500             505                 510
Val Lys Met Leu Lys Ser Asp Ala Thr Glu Lys Asp Leu Ser Asp Leu
        515             520                 525
Ile Ser Glu Met Glu Met Met Lys Met Ile Gly Lys His Lys Asn Ile
    530             535                 540
Ile Asn Leu Leu Gly Ala Cys Thr Gln Asp Gly Pro Leu Tyr Val Ile
545             550                 555                     560
Val Glu Tyr Ala Ser Lys Gly Asn Leu Arg Glu Tyr Leu Gln Ala Arg
                565                 570                 575
Arg Pro Pro Gly Leu Glu Tyr Cys Tyr Asn Pro Ser His Asn Pro Glu
            580                 585             590
Glu Gln Leu Ser Ser Lys Asp Leu Val Ser Cys Ala Tyr Gln Val Ala
        595             600                 605
Arg Gly Met Glu Tyr Leu Ala Ser Lys Lys Cys Ile His Arg Asp Leu
    610             615                 620
Ala Ala Arg Asn Val Leu Val Thr Glu Asp Asn Val Met Lys Ile Ala
625             630                 635                     640
Asp Phe Gly Leu Ala Arg Asp Ile His His Ile Asp Tyr Tyr Lys Lys
            645                 650                     655
Thr Thr Asn Gly Arg Leu Pro Val Lys Trp Met Ala Pro Glu Ala Leu
            660             665                 670
Phe Asp Arg Ile Tyr Thr His Gln Ser Asp Val Trp Ser Phe Gly Val
        675             680                 685
Leu Leu Trp Glu Ile Phe Thr Leu Gly Gly Ser Pro Tyr Pro Gly Val
    690             695                 700
Pro Val Glu Glu Leu Phe Lys Leu Leu Lys Glu Gly His Arg Met Asp
705             710                 715                     720
Lys Pro Ser Asn Cys Thr Asn Glu Leu Tyr Met Met Met Arg Asp Cys
            725             730                 735
Trp His Ala Val Pro Ser Gln Arg Pro Thr Phe Lys Gln Leu Val Glu
            740             745                 750
Asp Leu Asp Arg Ile Val Ala Leu Thr Ser Asn Gln Glu Tyr Leu Asp
        755             760                 765
Leu Ser Met Pro Leu Asp Gln Tyr Ser Pro Ser Phe Pro Asp Thr Arg
    770             775                 780
Ser Ser Thr Cys Ser Ser Gly Glu Asp Ser Val Phe Ser His Glu Pro
785             790                 795                     800
Leu Pro Glu Glu Pro Cys Leu Pro Arg His Pro Ala Gln Leu Ala Asn
            805                 810                     815
Arg Gly Leu Lys Glu Arg
            820
```

( 2 ) INFORMATION FOR SEQ ID NO:2:

( i ) SEQUENCE CHARACTERISTICS:
        ( A ) LENGTH: 2469 base pairs
        ( B ) TYPE: nucleic acid
        ( C ) STRANDEDNESS: unknown
        ( D ) TOPOLOGY: linear     ( i i ) MOLECULE TYPE: DNA (genomic)

( x i ) SEQUENCE DESCRIPTION: SEQ ID NO:2:

```
ATGTGGAGCT GGAAGTGCCT CCTCTTCTGG GCTGTGCTGG TCACAGCCAC ACTCTGCACC      60
GCTAGGCCGT CCCCGACCTT GCCTGAACAA GCCCAGCCCT GGGGAGCCCC TGTGGAAGTG     120
GAGTCCTTCC TGGTCCACCC CGGTGACCTG CTGCAGCTTC GCTGTCGGCT GCGGGACGAT     180
GTGCAGAGCA TCAACTGGCT GCGGGACGGG GTGCAGCTGG CGGAAAGCAA CCGCACCCGC     240
ATCACAGGGG AGGAGGTGGA GGTGCAGGAC TCCGTGCCCG CAGACTCCGG CCTCTATCCT     300
TGCGTAACCA GCAGCCCCTC GGGCAGTGAC ACCACCTACT TCTCCGTCAA TGTTTCAGAT     360
GCTCTCCCCT CCTCGGAGGA TGATGATGAT GATGATGACT CCTCTTCAGA GGAGAAAGAA     420
ACAGATAACA CCAAACCAAA CCGTATGCCC GTAGCTCCAT ATTGGACATC CCCAGAAAAG     480
ATGGAAAAGA AATTGCATGC AGTGCCGGCT GCCAAGACAG TGAAGTTCAA ATGCCCTTCC     540
AGTGGGACCC CAAACCCCAC ACTGCGCTGG TTGAAAAATG GCAAAGAATT CAAACCTGAC     600
CACAGAATTG GAGGCTACAA GGTCCGTTAT GCCACCTGGA GCATCATAAT GGACTCTGTG     660
GTGCCCTCTG ACAAGGGCAA CTACACCTGC ATTGTGGAGA ATGAGTACGG CAGCATCAAC     720
CACACATACC AGCTGGATGT CGTGGAGCGG TCCCCTCACC GGCCCATCCT GCAAGCAGGG     780
TTGCCCGCCA ACAAACAGT GGCCCTGGGT AGCAACGTGG AGTTCATGTG TAAGGTGTAC     840
AGTGACCCGC AGCCGCACAT CCAGTGGCTA AAGCACATCG AGGTGAATGG GAGCAAGATT     900
GGCCCAGACA ACCTGCCTTA TGTCCAGATC TTGAAGACTG CTGGAGTTAA TACCACCGAC     960
AAAGAGATGG AGGTGCTTCA CTTAAGAAAT GTCTCCTTTG AGGACGCAGG GGAGTATACG    1020
TGCTTGGCGG GTAACTCTAT CGGACTCTCC CATCACTCTG CATGGTTGAC CGTTCTGGAA    1080
GCCCTGGAAG AGAGGCCGGC AGTGATGACC TCGCCCCTGT ACCTGGAGAT CATCATCTAT    1140
TGCACAGGGG CCTTCCTCAT CTCCTGCATG GTGGGGTCGG TCATCGTCTA CAAGATGAAG    1200
AGTGGTACCA AGAAGAGTGA CTTCCACAGC CAGATGGCTG TGCACAAGCT GGCCAAGAGC    1260
ATCCCTCTGC GCAGACAGGT AACAGTGTCT GCTGACTCCA GTGCATCCAT GAACTCTGGG    1320
GTTCTTCTGG TTCGGCCATC ACGGCTCTCC TCCAGTGGGA CTCCCATGCT AGCAGGGGTC    1380
TCTGAGTATG AGCTTCCCGA AGACCCTCGC TGGGAGCTGC CTCGGGACAG ACTGGTCTTA    1440
GGCAAACCCC TGGGAGAGGG CTGCTTTGGG CAGGTGGTGT TGGCAGAGGC TATCGGGCTG    1500
GACAAGGACA AACCCAACCG TGTGACCAAA GTGGCTGTGA AGATGTTGAA GTCGGACGCA    1560
ACAGAGAAAG ACTTGTCAGA CCTGATCTCA GAAATGGAGA TGATGAAGAT GATCGGGAAG    1620
CATAAGAATA TCATCAACCT GCTGGGGGCC TGCACGCAGG ATGGTCCCTT GTATGTCATC    1680
GTGGAGTATG CCTCCAAGGG CAACCTGCGG GAGTACCTGC AGGCCCGGAG GCCCCCAGGG    1740
CTGGAATACT GCTACAACCC CAGCCACAAC CCAGAGGAGC AGCTCTCCTC CAAGGACCTG    1800
GTGTCCTGCG CCTACCAGGT GGCCCGAGGC ATGGAGTATC TGGCCTCCAA GAAGTGCATA    1860
CACCGAGACC TGGCAGCCAG GAATGTCCTG GTGACAGAGG ACAATGTGAT GAAGATAGCA    1920
GACTTTGGCC TCGCACGGGA CATTCACCAC ATCGACTACT ATAAAAAGAC AACCAACGGC    1980
CGACTGCCTG TGAAGTGGAT GGCACCCGAG GCATTATTTG ACCGGATCTA CACCCACCAG    2040
AGTGATGTGT GGTCTTTCGG GGTGCTCCTG TGGGAGATCT TCACTCTGGG CGGCTCCCCA    2100
```

| TACCCCGGTG | TGCCTGTGGA | GGAACTTTTC | AAGCTGCTGA | AGGAGGGTCA | CCGCATGGAC | 2160 |
| AAGCCCAGTA | ACTGCACCAA | CGAGCTGTAC | ATGATGATGC | GGGACTGCTG | GCATGCAGTG | 2220 |
| CCCTCACAGA | GACCCACCTT | CAAGCAGCTG | GTGGAAGACC | TGGACCGCAT | CGTGGCCTTG | 2280 |
| ACCTCCAACC | AGGAGTACCT | GGACCTGTCC | ATGCCCTGG | ACCAGTACTC | CCCCAGCTTT | 2340 |
| CCCGACACCC | GGAGCTCTAC | GTGCTCCTCA | GGGGAGGATT | CCGTCTTCTC | TCATGAGCCG | 2400 |
| CTGCCCGAGG | AGCCCTGCCT | GCCCCGACAC | CCAGCCCAGC | TTGCCAATCG | GGGACTCAAA | 2460 |
| CGCCGCTGA | | | | | | 2469 |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: linear     ( i i ) MOLECULE TYPE: DNA (genomic)

( x i ) SEQUENCE DESCRIPTION: SEQ ID NO:3:

| ATAACGGACC | TTGTAGCCTC | CAATTCTGTG | 30 |

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: linear     ( i i ) MOLECULE TYPE: DNA (genomic)

( x i ) SEQUENCE DESCRIPTION: SEQ ID NO:4:

| GGGTCTCTGT | GAGGGCACTG | CATGCCAGCA | 30 |

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: linear     ( i i ) MOLECULE TYPE: DNA (genomic)

( x i ) SEQUENCE DESCRIPTION: SEQ ID NO:5:

| ACGGCCTAGC | GGTGCAGAGT | GTGGCTGTGA | 30 |

( 2 ) INFORMATION FOR SEQ ID NO:6:

( i ) SEQUENCE CHARACTERISTICS:
        ( A ) LENGTH: 146 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:6:

| AGCTTGGGCA | TACATTCAAT | CAATTGTTAT | CTAAGGAAAT | ACTTACATAT | GGCTAGGCCG | 60 |
| TCCCCGACCT | TGCCTGAACA | AGCCCAGCCC | TGGGGAGCCC | CTGTGGAAGT | GGAGTCCTTC | 120 |
| CTGGTCCACC | CCGGTGACCT | GCTGCA | | | | 146 |

( 2 ) INFORMATION FOR SEQ ID NO:7:

(i) SEQUENCE CHARACTERISTICS:
  (A) LENGTH: 17 base pairs
  (B) TYPE: nucleic acid
  (C) STRANDEDNESS: unknown
  (D) TOPOLOGY: linear (ii) MOLECULE TYPE: DNA (genomic)

(xi) SEQUENCE DESCRIPTION: SEQ ID NO:7:

GTAAAACGAC GGCCAGT                                                17

(2) INFORMATION FOR SEQ ID NO:8:

(i) SEQUENCE CHARACTERISTICS:
    (A) LENGTH: 36 base pairs
    (B) TYPE: nucleic acid
    (C) STRANDEDNESS: unknown
    (D) TOPOLOGY: linear (ii) MOLECULE TYPE: DNA (genomic)

(xi) SEQUENCE DESCRIPTION: SEQ ID NO:8:

ATGAGGATCC TCACTCCAGG TACAGGGGCG AGGTCA                            36